United States Patent [19]
Gaffar et al.

[11] 4,224,308
[45] Sep. 23, 1980

[54] ANTICALCULUS ORAL COMPOSITION

[75] Inventors: Abdul Gaffar, Somerset; John J. Grecsek, Trenton, both of N.J.

[73] Assignee: Colgate-Palmolive Company, New York, N.Y.

[21] Appl. No.: 69,463

[22] Filed: Aug. 24, 1979

[51] Int. Cl.² .................................................. A61K 7/16
[52] U.S. Cl. ........................................................ 424/49
[58] Field of Search ........................................ 424/49–58

[56] References Cited

U.S. PATENT DOCUMENTS

| Re. 29,182 | 4/1977 | McCune et al. | 424/54 |
| 3,553,315 | 1/1971 | Francis | 424/49 |
| 3,678,154 | 7/1972 | Widder et al. | 424/52 |
| 3,886,204 | 5/1975 | Geffers et al. | 260/502.4 R |
| 3,886,205 | 5/1975 | Geffers et al. | 260/502.4 R |
| 3,934,002 | 1/1976 | Haefele | 424/54 |
| 3,959,458 | 5/1976 | Agricola et al. | 424/52 |
| 4,025,616 | 5/1977 | Haefele | 424/52 |
| 4,077,997 | 3/1978 | Blum et al. | 424/49 X |
| 4,118,474 | 10/1978 | Gaffar et al. | 424/54 |
| 4,118,476 | 10/1978 | Gaffar et al. | 424/54 |

Primary Examiner—Shep K. Rose
Attorney, Agent, or Firm—Herbert S. Sylvester; Murray M. Grill; Norman Blumenkopf

[57] ABSTRACT

An oral composition effective to promote oral hygiene containing as an anticalculus agent a 2-phosphonobutane-1,2,4-tricarboxylic acid compound or an orally acceptable salt thereof.

7 Claims, No Drawings

ARTICALCULUS ORAL COMPOSITION

This invention relates to oral compositions containing an anticalculus agent.

Calculus is a hard, mineralized formation which forms on the teeth. Regular brushing prevents a rapid build-up of these deposits, but even regular brushing is not sufficient to remove all of the calculus deposits which adhere to the teeth. Calculus is formed on the teeth when crystals of calcium phosphates begin to be deposited in the pellicle and extracellular matrix of the dental plaque and become sufficiently closely packed together for the aggregates to become resistant to deformation. There is no complete agreement on the route by which calcium and orthophosphate ultimately become the crystalline material called hydroxyapatite (HAP). It is generally agreed, however, that at higher saturations, that is, above the critical saturation limit, the precursor to crystalline hydroxyapatite is an amorphous or microcrystalline calcium phosphate. "Amorphous calcium phosphate" although related to hydroxyapatite differs from it in atomic structure, particle morphology, and stoichiometry. The X-ray diffraction pattern of amorphous calcium phosphate shows broad peaks typical of amorphous materials, which lack the long-range atomic order characteristics of all crystalline materials, including hydroxyapatite. It is apparent therefore that agents which effectively interfere with crystalline growth of hydroxyapatite will be effective as anticalculus agents. A suggested mechanism by which the anticalculus agents of this invention inhibit calculus formation probably involves an increase of the activation energy barrier thus inhibiting the transformation of precursor amorphous calcium phosphate to hydroxyapatite.

Studies have shown that there is a good correlation between the ability of a compound to prevent hydroxyapatite crystalline growth in vitro and its ability to prevent calcification in vivo.

A substantial number of different types of compounds and compositions have been developed for use as antibacterial, and antiplaque and anticalculus agents in oral compositions, including for example such cationic materials as the bisbiguanide compounds and quaternary ammonium compounds, e.g. benzethonium chloride and cetyl pyridinium chloride, disclosed in U.S. Pat. No 4,110,429. These cationic materials however tend to stain the teeth with continued use.

It is an object of this invention to provide an improved anticalculus oral composition which will have relatively little or no tendency to stain the teeth.

A further object of the invention is to provide an oral composition which inhibits the transformation of amorphous calcium phosphate to hydroxyapatite crystal structure normally associated with calculus.

Another object of this invention is the provision of an improved method for inhibiting the formation of calculus.

Other objects and advantages will appear as the description proceeds.

In accordance with certain of its aspects, this invention relates to an oral composition comprising oral (orally acceptable) vehicle containing in an effective amount as an anticalculus agent a 2-phosphono-butane-1,2,4-tricarboxylic acid (PBTA) compound, of the formula

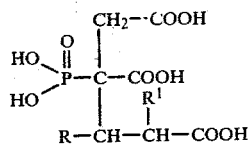

wherein R is hydrogen, lower alkyl or carboxyl, and $R^1$ is hydrogen or methyl, or an orally acceptable salt thereof, preferably water soluble, such as with an alkali metal (e.g. sodium and potassium), ammonium, $C_1$–$C_{18}$ mono-, di- and tri-substituted ammonium (e.g. alkanol substituted such as mono-, di- and tri-ethanolammonium) cation.

Compounds of the above formula, and methods for their production, are disclosed in U.S. Pat. Nos. 3,886,204 and 3,886,205, which disclosures are incorporated herein by reference thereto. The preferred PBTA compound for use in the present invention is the unsubstituted compound of the above formula (I) in which R and $R^1$ are each hydrogen. When R is lower alkyl, it preferably contains 1 to 4 carbon atoms, especially methyl.

The concentration of the PBTA compound (or salt) in the oral compositions can range widely, typically upward from about 0.01% by weight, with no upper limit on the amount that can be utilized except as dictated by cost or incompatibility with the vehicle. Generally, concentrations from about 0.01% to about 10% and preferably about 0.1% to about 3% by weight are utilized. Oral compositions which in the ordinary course of usage could be accidentally ingested preferably contain lower concentrations of the PBTA compound. Thus, a mouthwash in accordance with this invention preferably contains less than about 1.5% by weight of the PBTA compound. Other dentifrice compositions, topical solutions and prophylactic pastes, the latter to be administered professionally, can preferably contain about 0.1% to 2% by weight of the PBTA compound.

The PBTA compounds of this invention are antinucleating agents, oral compositions of this invention containing them are effective in reducing formation of dental calculus without unduly decalcifying the dental enamel, and in contrast to the above-mentioned cationic antibacterial, antiplaque and anti-calculus agents, such PBTA compounds and compositions have little or no tendency to stain the teeth.

The PBTA compounds and compositions of this invention have additionally been found to effectively reduce or inhibit gingivitis.

In certain highly preferred forms of the invention the oral composition may be substantially liquid in character, such as a mouthwash or rinse. In such a preparation the vehicle is typically a water-alcohol mixture desirably including a humectant as described below. Generally, the ratio of water to alcohol is in the range of from about 1:1 to about 20:1, preferably about 3:1 to 10:1 and most preferably about 4:1 to about 5:1, by weight. The total amount of water-alcohol mixture in this type of preparation is typically in the range of from about 70% to about 99.9% by weight of the preparation. The pH of such liquid and other preparations of the invention is generally in the range of from about 4.5 to about 9 and typically from about 5.5 to 8. The pH is preferably in the range of from about 6 to about 8.0. It is noteworthy that the compositions of the invention may be applied orally at a pH below 5 without substantially decalcifying dental enamel. The pH can be controlled with acid (e.g. citric acid or benzoic acid) or base (e.g. sodium hydroxide) or buffered (as with phosphate buffers). Such liquid oral preparations may also contain a surface active agent and/or a fluorine-providing compound.

In certain other desirable forms of this invention, the oral composition may be substantially solid or pasty in character, such as toothpowder, a dental tablet, a toothpaste or dental cream. The vehicle of such solid or pasty oral preparations generally contains polishing material. Examples of polishing materials are water-insoluble sodium metaphosphate, potassium metaphosphate, tricalcium phosphate, dihydrated calcium phosphate, anhydrous dicalcium phosphate, calcium pyrophosphate, magnesium orthophosphate, trimagnesium phosphate, calcium carbonate, alumina, hydrated alumina, aluminum silicate, zirconium silicate, silica, bentonite, and mixtures thereof. Preferred polishing materials include silica gel or colloidal silica, complex amorphous alkali metal aluminosilicate and hydrated alumina.

Alumina, particularly the hydrated alumina sold by Alcoa as C333, which has an alumina content of 64.9% by weight, a silica content of 0.008%, a ferric oxide content of 0.003%, and a moisture content of 0.37%, at 110° C., and which has a specific gravity of 2.42 and a particle size such that 100% of the particles are less than 50 microns and 84% of the particles are less than 20 microns, is very effective.

When visually clear gels are employed, a polishing agent of colloidal silica, such as those sold under the trademark SYLOID as Syloid 72 and Syloid 74 or under the trademark SANTOCEL as Santocel 100 and alkali metal aluminosilicate complexes are particularly useful, since they have refractive indices close to the refractive indices of gelling agent-liquid (including water and/or humectant) systems commonly used in dentifrices.

Many of the so-called "water-insoluble" polishing materials are anionic in character and also include small amounts of soluble material. Thus, insoluble sodium metaphosphate may be formed in any suitable manner, as illustrated by Thorpe's *Dictionary of Applied Chemistry*, Volume 9, 4th Edition, pp. 510-511. The forms of insoluble sodium metaphosphate known as Madrell's salt and Kurrol's salt are further examples of suitable materials. These metaphosphate salts exhibit a minute solubility in water, and therefore are commonly referred to as insoluble metaphosphates. There is present therein a minor amount of soluble phosphate material as impurities, usually a few percent such as up to 4% by weight. The amount of soluble phosphate material, which is believed to include a soluble sodium trimetaphosphate in the case of insoluble metaphosphate, may be reduced by washing with water if desired. The insoluble alkali metal metaphosphate is typically employed in powder form of a particle size such that no more than about 1% of the material is larger than about 37 microns.

The polishing material is generally present in amounts ranging from about 10% to about 99% by weight of the oral preparation. Preferably, it is present in amounts ranging from about 10% to about 75% in toothpaste, and from about 70% to about 99% in toothpowder.

In the preparation of toothpowders, it is usually sufficient to admix mechanically, e.g., by milling, the various solid ingredients in appropriate quantities and particle sizes.

In pasty oral preparations the PBTA compound should be compatible with the other components of the preparation. Thus, in a toothpaste, the liquid vehicle may comprise water and humectant typically in an amount ranging from about 10% to about 90% by weight of the preparation. Glycerine, propylene glycol, sorbitol, or polyethylene glycol 400 may also be present as humectants or binders. Particularly advantageous liquid ingredients comprise mixtures of water, glycerine and sorbitol.

In clear gels where the refractive index is an important consideration, about 3-30% by weight of water, 0 to about 80% by weight of glycerine, and about 20-80% by weight of sorbitol is preferably employed. A gelling agent, such as natural or synthetic gums or gum-like materials, typically Irish moss, sodium carboxymethylcellulose, methyl cellulose, or hydroxyethyl cellulose, may be employed. Other gelling agents which may be employed include gum tragacanth, polyvinylpyrrolidone and starch. They are usually present in toothpaste in an amount up to about 10% by weight, preferably in the range of from about 0.5% to about 5%. The preferred gelling agents are methyl cellulose and hydroxyethyl cellulose. In a toothpaste or gel, the liquids and solids are proportioned to form a creamy or gelled mass which is extrudable from a pressurized container or from a collapsible, e.g., aluminum or lead, tube.

The solid or pasty oral preparation which typically has a pH measured on a 20% slurry of about 4.5 to 9, generally about 5.5 to about 8 and preferably about 6 to about 8.0, may also contain a surface active agent and/or a fluorine-providing compound.

It will be understood that, as is conventional, the oral preparations are to be sold or otherwise distributed in suitable labelled packages. Thus a jar of mouthrinse will have a label describing it, in substance, as a mouthrinse or mouthwash and having directions for its use; and a toothpaste will usually be in a collapsible tube, typically aluminum, lined lead or plastic, or other squeeze dispenser for metering out the contents, having a label describing it, in substance, as a toothpaste or dental cream.

Organic surface-active agents are used in the compositions of the present invention to achieve increased prophylactic action, assist in achieving thorough and complete dispersion of the anticalculus agent throughout the oral cavity, and render the instant compositions more cosmetically acceptable. The organic surface-active material is preferably anionic, nonionic or ampholytic in nature, and it is preferred to employ as the surface-active agent a detersive material which imparts to the composition detersive and foaming properties. Suitable examples of anionic surfactants are water-soluble salts of higher fatty acid monoglyceride monosulfates, such as the sodium salt of the monosulfated monoglyceride of hydrogenated coconut oil fatty acids, higher alkyl sulfates, such as sodium lauryl sulfate, alkyl aryl sulfonates, such as sodium dodecyl benzene sulfonate, higher alkyl sulfoacetates, higher fatty acid esters of 1,2 dihydroxy propane sulfonate, and the substantially saturated higher aliphatic acyl amides of lower aliphatic amino carboxylic acid compounds, such as those having 12 to 16 carbons in the fatty acid, alkyl, or acyl radicals, and the like. Examples of the last mentioned amides are N-lauroyl sarcosine, and the sodium, potassium, and ethanolamine salts of N-lauroyl, N-myristoyl, or N-palmitoyl sarcosine which should be substantially free from soap or similar higher fatty acid material. The use of these sarcosinate compounds in dentifrice compositions of the present invention is particularly advantageous since these materials exhibit a prolonged and marked effect in the inhibition of acid formation in the oral cavity due to carbohydrate breakdown in addition to exerting some reduction in the solubility of tooth enamel in acid solutions.

Examples of water-soluble nonionic surfactants are condensation products of ethylene oxide with various reactive hydrogen-containing compounds reactive therewith having long hydrophobic chains (e.g. aliphatic chains of about 12 to 20 carbon atoms), which condensation products ("ethoxamers") contain hydrophilic polyoxyethylene moieties, such as condensation products of poly (ethylene oxide) with fatty acids, fatty alcohols, fatty amides, polyhydric alcohols (e.g. sorbitan monosterate) and polypropyleneoxide (i.e. Pluronic materials).

In certain forms of this invention a fluorine-providing compound is present in the oral preparation. These compounds may be slightly soluble in water or may be fully water-soluble. They are characterized by their ability to release fluoride ions in water and by substantial freedom from reaction with other compounds of the oral preparation. Among these materials are inorganic fluoride salts, such as soluble alkali metal, alkaline earth metal and heavy metal salts, for example, sodium fluoride, potassium fluoride, ammonium fluoride, a copper fluoride such as cuprous fluoride, zinc fluoride, a tin fluoride such as stannic fluoride or stannous chlorofluoride, barium fluoride, sodium fluorsilicate, ammonium fluorosilicate, sodium fluorozirconate, sodium monofluorophosphate, aluminum mono- and di-fluorophosphate, and fluorinated sodium calcium pyrophosphate. Alkali metal and tin fluorides, such as sodium and stannous fluorides, sodium monofluorophosphate and mixtures thereof, are preferred.

The amount of the fluorine-providing compound is dependent to some extent upon the type of compound, its solubility, and the type of oral preparation, but it must be a nontoxic amount. In a solid oral preparation, such as toothpaste or toothpowder, an amount of such compound which releases a maximum of about 1% by weight of the preparation is considered satisfactory. Any suitable minimum amount of such compound may be used, but it is preferably to employ sufficient compound to release about 0.005% to 1%, and preferably about 0.1% of fluoride ion. Typically, in the cases of alkali metal fluorides and stannous fluoride, this component is present in an amount up to about 2% by weight, based on the weight of the preparation, and preferably in the range of about 0.05% to 1%. In the case of sodium monofluorophosphate, the compound may be present in an amount up to 7.6% by weight, more typically about 0.76%.

In a liquid oral preparation such as a mouthwash, the fluorine-providing compound is typically present in an amount sufficient to release up to about 0.13%, preferably about 0.0013% to 0.1% and most preferably about 0.0013% to 0.5%, by weight, of fluoride ion.

Various other materials may be incorporated in the oral preparations of this invention such as whitening agents, preservatives, silicones, chlorophyll compounds, other anticalculus agents, antibacterial antiplaque agents, and/or ammoniated material such as urea, diammonium phosphate, and mixtures thereof. These adjuvants, where present, are incorporated in the preparation in amounts which do not substantially adversely affect the properties and characteristics desired.

Any suitable flavoring or sweetening material may also be employed. Examples of suitable flavoring or sweetening material may also be employed. Examples of suitable flavoring constituents are flavoring oils, e.g., oil of spearmint, peppermint, wintergreen, sassafras, clove, sage, eucalyptus, marjoram, cinnamon, lemon, and orange, and methyl salicylate. Suitable sweetening agents include sucrose, lactose, maltose, sorbitol, xylitol, sodium cyclamate, perillartine, APM (aspartyl phenylanine, methyl ester), saccharine and the like. Suitably, flavor and sweetening agents may together comprise from about 0.01% to 5% or more of the preparation.

In preparing the oral compositions of this invention, it is preferred but not essential to add the PBTA after the other ingredients (except perhaps some of the water) are mixed or contacted with each other to avoid a tendency for the PBTA to be precipitated.

For instance, a mouthrinse or mouthwash may be prepared by mixing ethanol and water with flavoring oil, surfactant, humectant, gum or thickener such as sodium carboxymethylcellulose or hydroxyethyl cellulose, and sweetener and adding thereto polishing agent, flavor, additional water, and then the PBTA compound.

In the practice of this invention an oral composition according to this invention such as a mouthwash or toothpaste containing the PBTA compound in an amount effective to inhibit calculus on dental surfaces is applied regularly to dental enamel, preferably from about 5 times per week to about 3 times daily, at a pH of about 4.5 to about 9, generally about 5.5 to about 8, preferably about 6 to 8.

The following examples are further illustrative of the nature of the present invention, but it is understood that the invention is not limited thereto. All amounts and proportions referred to herein and in the appended claims are by weight unless otherwise indicated.

EXAMPLE 1

Inhibition of Crystal Growth of HAP

This is evaluated by a pH Stat method. 1.0 ml of an aqueous solution of $1 \times 10^{-4}$ M to $1 \times 10^{-5}$ M of the anticalculus agent being tested and 0.1 M sodium dihydrogen phosphate is placed in a reaction flask with 22 to 23 ml. of distilled water with continuous stirring in an atmosphere of nitrogen. To this is added 1 ml. of 0.1 M $CaCl_2$ and the pH adjusted to $7.4 \pm 0.05$ with NaOH (final conc. of $Ca^{++}$ and $PO_4^{3-} = 4 \times 10^{-3}$ M). Consumption of 0.1 N NaOH is recorded automatically by a pH Stat (Radiometer). In this test, the formation of HAP occurs in 2 distinct phases. First rapid base consumption (1-4 min.) then diminishes until 15-20 minutes when second rapid uptake takes place. A delay in the time of second rapid consumption or a total absence of the second rapid consumption indicates an interference with the crystal growth of HAP. Agents which interfere with HAP crystal growth are effective anticalculus agents. When PBTA is tested by the foregoing procedure, the following results are obtained.

| Anticalculus Agent (conc) | Time for HAP Formation | Delay in HAP Formation |
|---|---|---|
| Water (control) | 15 min. | — |
| PBTA (4 ppm) | 25 min. | 10 min. |
| PBTA (8 ppm) | 75 min. | 60 min. |
| PBTA (10 ppm) | 129 min. | 114 min. |
| PBTA (20 ppm) | 33.8 hrs. | |

The above results show that PBTA effectively inhibits crystal growth of HAP in vitro and that the inhibition is not due to complexation or chelation of calcium since sub-stoichiometric ratios of PBTA:calcium are employed.

In the following examples illustrative of mouthwash formulations according to the invention, Pluronic F108 is a polyoxyalkylene block polymer.

| | Example | | | |
|---|---|---|---|---|
| | 2 | 3 | 4 | 5 |
| Flavor | 0.22% | 0.22% | 0.22% | 0.22% |
| Ethanol | 15.0 | 15.0 | 15.0 | 15.0 |
| Pluronic F108 | 3.0 | 3.0 | 3.0 | 3.0 |
| Glycerine | 10.0 | 10.0 | 10.0 | 10.0 |
| Na Saccharin | 0.03 | 0.03 | 0.03 | 0.03 |
| PBTA | 0.1 | 0.2 | 0.5 | 1.0 |
| Water q.s. to | 100 | 100 | 100 | 100 |
| pH (with NaOH) | 7.4 | 7.4 | 7.4 | 7.4 |
| Appearance | Clear | Clear | Clear | Clear |

The following examples are illustrative of anticalculus toothpastes according to the invention:

| | Example | |
|---|---|---|
| | 6 | 7 |
| Silica | 30 | 30 |
| Glycerine | 16 | 16 |
| Sorbitol (70%) | 6 | 6 |
| Pluronic F-108 | 3 | 3 |
| Hydroxyethyl cellulose | 1.2 | 1.2 |
| PBTA | 2 | 2 |
| Sodium saccharin | 0.17 | 0.17 |
| Flavor | 0.8 | 0.8 |
| Water q.s. to | 100 | 100 |

This invention has been described with respect to preferred embodiments and it will be understood that modifications and variations thereof obvious to those skilled in the art are to be included within the spirit and purview of this application and the scope of the appended claims.

What we claim is:

1. An oral composition comprising an orally acceptable vehicle containing in an effective amount as an anticalculus agent a 2-phosphono-butane-1,2,4-tricarboxylic acid compound of the formula

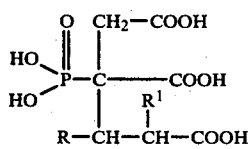

wherein R is hydrogen, lower alkyl or carboxyl, and $R^1$ is hydrogen or methyl, or an orally acceptable salt thereof.

2. The oral composition of claim 1 wherein R and $R^1$ are hydrogen.

3. The oral composition of claims 1 or 2 wherein said agent is present in amount of about 0.01% to about 10% by weight.

4. The oral composition of claims 1 or 2 wherein said vehicle is an aqueous-alcohol and said composition is a mouthwash of pH of about 4.5 to about 9.

5. The oral composition of claims 1 or 2 wherein said vehicle comprises a liquid vehicle, a gelling agent and a dentally acceptable polishing material, and said composition is a toothpaste of pH of about 4.5 to about 9.

6. A method of inhibiting the formation of dental calculus comprising applying to teeth a calculus-inhibiting amount of a composition as defined in claim 1.

7. A method of inhibiting the formation of dental calculus comprising applying to teeth a calculus-inhibiting amount of a composition as defined in claim 2.